(12) United States Patent
James

(10) Patent No.: US 7,465,287 B2
(45) Date of Patent: Dec. 16, 2008

(54) APPARATUS FOR DISPENSING POWDERED MATERIAL

(75) Inventor: Michael H. James, Ramsey (GB)

(73) Assignee: Nasaleze Patents Limited, Ramsey (IM)

(*) Notice: Subject to any disclaimer, the term of this patent is extended or adjusted under 35 U.S.C. 154(b) by 127 days.

(21) Appl. No.: 10/467,773

(22) PCT Filed: Feb. 8, 2002

(86) PCT No.: PCT/GB02/00553

§ 371 (c)(1),
(2), (4) Date: Aug. 7, 2003

(87) PCT Pub. No.: WO02/062416

PCT Pub. Date: Aug. 15, 2002

(65) Prior Publication Data

US 2004/0082907 A1    Apr. 29, 2004

(30) Foreign Application Priority Data

Feb. 8, 2001   (GB) .................. 0103172.3
Mar. 19, 2001  (GB) .................. 0106789.1

(51) Int. Cl.
*A61M 13/00* (2006.01)

(52) U.S. Cl. ........................................ 604/58

(58) Field of Classification Search ............ 604/57–60, 604/36, 37, 77, 212, 216, 217, 275, 310; 128/200.14, 200.16, 200.18, 200.19, 200.22, 128/200.23; 222/173, 211–215, 491, 494, 222/150, 151, 633, 95

See application file for complete search history.

(56) References Cited

U.S. PATENT DOCUMENTS

| 443,545 | A | * | 12/1890 | Rowland | 128/203.15 |
| 464,969 | A | * | 12/1891 | Ives | 128/203.15 |
| 2,796,294 | A | | 6/1957 | McKinnon | |
| 2,896,825 | A | * | 7/1959 | Jackson | 222/211 |
| 3,100,362 | A | * | 8/1963 | Robinette | 222/211 |
| 3,241,726 | A | * | 3/1966 | Chester | 222/211 |
| 3,572,590 | A | | 3/1971 | Malone | |
| 3,666,182 | A | | 5/1972 | Cureton | |
| 4,015,753 | A | * | 4/1977 | Bennett | 222/633 |
| 4,730,751 | A | * | 3/1988 | Mackles et al. | 222/211 |
| 5,584,417 | A | | 12/1996 | Graf et al. | |

(Continued)

FOREIGN PATENT DOCUMENTS

EP    0 972 533    7/1999

(Continued)

*Primary Examiner*—Kevin C Sirmons
*Assistant Examiner*—Catherine N Witczak
(74) *Attorney, Agent, or Firm*—Wilmer Cutler Pickering Hale and Dorr LLP

(57) ABSTRACT

The invention relates to an apparatus for dispensing a restricted amount of powdered material, comprising a repository (2) for powdered material (4), an outlet (12), and a conduit (3). The apparatus defines an airway arranged to enable air to be drawn through the resting powdered material in the repository, thereby entraining the powdered material in the airflow and drawing the air and entrained powdered material through the conduit. The air and entrained powdered material is thereafter expelled out of the outlet. Additionally, the invention relates to a dip tube (3) for use in apparatus for dispensing a powdered material.

20 Claims, 4 Drawing Sheets

U.S. PATENT DOCUMENTS 5,683,361 A    11/1997  Elk et al.
5,884,621 A *   3/1999  Matsugi et al. ........ 128/203.15
5,971,234 A * 10/1999  Mathison et al. ............ 222/633
6,647,980 B1 * 11/2003  Gizurarson ............ 128/200.14

FOREIGN PATENT DOCUMENTS

FR    2628638 A1   4/1989
GB     627662     8/1949
GB     806284    12/1958

* cited by examiner

APPARATUS FOR DISPENSING POWDERED MATERIAL

This application is a national stage entry of PCT/GB02/00553, filed Feb. 8, 2002, and also claims priority under 35 U.S.C. §119 to applications GB0103172.3, filed Feb. 8, 2001 and GB0106789.1, filed Mar. 19, 2001.

The present invention relates to apparatus for dispensing a restricted or regulated amount of powdered material and component parts. Apparatus of this type are particularly useful in the delivery of powdered material to the human nasal tract.

The dispensing of powdered materials, both pharmaceutically active and non-pharmaceutically active, is required for a number of uses. Talcum powders are put on the skin to make it feel smooth or to help it stay dry. A number of anti-fungal treatments, for both plants and animals, are dispensed in powdered form, i.e. powdered preparations for "athletes foot". Powders are delivered to the lungs or nasal membrane in the form of a spray or an aerosol for a number of therapeutic purposes.

The topical treatment of asthma, by the application of regulated amounts of powdered medicaments to the lungs, has become a well established practice. Although not so well established, it is also known to treat allergic rhinitis (hayfever) with powdered medicaments applied to the nasal membranes. So treating these and similar conditions can give rise to various advantages. Firstly, any pharmaceutically active component of a powder administered in this way can take effect quickly as, unlike with oral preparations, there is no need for it to be absorbed via the gastro-intestinal tract before being transported to the lungs or nasal cavity. Secondly, these techniques allow 'first-pass' effects to be avoided and, thirdly, since the powder is applied at the site where it is required, their use reduces the systemic dosage of active agent (when present) and, hence, any risk of undesirable side effects.

As well as directly treating the epithelial cells lining the nose or lungs, powdered material can also be delivered to the nose or lungs as a means of conveying an active agent directly to the blood stream.

Powdered materials are often delivered to the lungs or nasal membranes in the form of a spray or an aerosol produced by an inhaler or like device. There are several main types of inhaler device currently available on the market. These include metered dose inhalers and the devices sold under the trademarks Diskhaler® and Rotahaler®. In the case of metered dose inhalers, the powder for delivery is contained in a pressurised canister and activating a valve on the canister causes a defined amount of the powder to be released in a jet of propellant gas. Diskhalers®, on the other hand, accept magazines, each in the form of a blister pack in which each blister contains an individual dose consisting of a defined amount of powder. To operate the device, the user must align a loaded blister within the device, pierce it to release the powder and then suck the released powder into his lungs. Rotahalers® are similar, but accept single capsules of powder.

Diskhalers® and Rotahalers® require a plurality of manipulations in order not only to load them, but also to have them release a pre-measured quantity of material, before it is available for inhalation by the user. The level of manual dexterity required to use these devices makes them particularly unsuited to use by the very young, infirm, handicapped and old. The effective use of a metered dose inhaler requires an ability to co-ordinate inhalation with valve actuation that is beyond the capacity of many potential users, particularly the very young.

The above discussed known devices are relatively complex pieces of apparatus, all of which include a number of intricate moving parts. This, in turn, makes them expensive to manufacture and easy to break. They are also sufficiently prone to clogging to require cleaning on a daily basis. However, they do have the advantage that they are able to dispense a predetermined dose.

Although simple devices for the delivery of powdered material exist, none are capable of restricting the level of powdered material that is dispensed. Such simple devices comprise a container for the powder and an amount of the powder to be dispensed, only loosely controlled by a simple hole, or a large gauze or open cell foam plug. In use, these devices are inverted and the powder allowed to freely flow downwards, doing little to restrict the flow of the powdered material. Such devices are adequate for dispensing non-pharmaceutically active compounds, or therapeutically active compounds with a wide therapeutic window, which do not require precise regulation of dosage, negating the need to use expensive and complexes devices described. These devices have the advantage that they are cheap to manufacture and easy to use. However, the amount of powder dispensed is not regulated which is wasteful and therefore unduly costly.

Additionally, as these devices must be inverted for the powdered material to be delivered, it is difficult to deliver the powder to the axilla, or orifices such as the nasal cavity. Where powder is to be delivered to the axilla, or the nasal cavity, one must adopt an uncomfortable position before inversion of the device, i.e. when delivering powder to the nasal cavity, the head must be bent backwards.

It is an object of the present invention to provide a simple apparatus which will regulate, to an extent, the amount of powder delivered, which improves upon apparatus already in use.

In an embodiment of the invention a deformable bottle contains some powdered material and houses a dip tube. Squeezing the sides of the bottle, by opposing fingers, increases the internal pressure of the bottle when compared to atmospheric pressure resulting in an airflow that is channelled out of the bottle through the dip tube. This airflow entrains the powdered material, releasing a restricted amount of the powdered material from the bottle.

In a preferred embodiment the powder is hydroxypropylmethylcellulose, an inert cellulose powder. When delivered into the nasal cavity it immediately turns to a gel-like material as it reacts with the moisture present in the nasal tract. This gel is able to replicate the properties of real mucus and as such is able to alleviate, prevent or ultimately stop a hayfever or asthma attack.

Epithelial cells lining the nasal tract contain a secretion called mucus, which accumulates in the cells giving them a distended and goblet-shaped appearance. Eventually, the goblet cells burst releasing the mucus, which as well as protecting the nasal membranes from mechanical and chemical injury also prevents inhaled particles from reaching the delicate alveoli of the lungs.

Allergens entrained in air inhaled into the nasal tract, alight on the mucus present therein, whereby, because of the mucus's low surface tension, they are immediately adsorbed. The shape of the nasal tract causes a "smoke ring" effect to occur so that dust, dirt, pollen etc. is instantly separated out from and pushed to the periphery of the clear air left in the middle. This clean air is then able to enter the lungs while the mucus, which eventually drains out naturally through the digestive system, adsorbs the allergens. People who suffer with allergic rhinitis and asthma often have a reduced amount of mucus.

The dispensing of hydroxypropylmethylcellulose to the nasal cavity, in order to mimic mucus, does not require a precise dosage as the compound is pharmaceutically inert. However, an unrestricted delivery of the powder may cause an uncomfortable blockage of the nasal cavity and may even result in difficulty in breathing through the nose. Furthermore, delivery of amounts of the powdered material that exceeds a volume that is required for the powder to be effective, is wasteful and therefore unduly costly.

Accordingly, in a first aspect of the invention, there is provided apparatus for dispensing a restricted amount of powdered material, comprising a repository for powdered material, an outlet and a passageway defined between the repository and the outlet, wherein a volume of air can be propelled through powdered material resting in the repository, thereby entraining powdered material, and carry powdered material thus entrained along the passageway and out of the apparatus in an upwardly direction, via the outlet.

In a preferred embodiment a restriction in the passageway regulates the amount of powdered material delivered.

In a further preferred embodiment a conduit extends between the repository and the outlet, and defines the restriction. Preferably an entrance to the conduit is defined within the repository and said restriction is disposed at said entrance. More preferably, the restriction is produced by a gap defined between said entrance and a wall of the repository. The conduit can comprise a tube with an open end in substantial abutment with a wall of the repository and the restriction can be provided by an opening in the wall of said tube. The opening can be in the form of one or more notches in the open end of the tube.

It was noted during development of the apparatus in accordance with the invention, that during manufacture of the apparatus, insertion of the dip tube resulted in the compression of the powder beneath the flat surface of the rim at the end of the dip tube, ultimately resulting in a blockage of the airway and making it difficult to fully insert the dip tube. Effective insertion of the dip tube into the apparatus was only capable of being effected when the apparatus was on its side. Manufacture of the apparatus in this orientation is difficult as the powdered material may easily pour out of the apparatus, thus rendering the manufacturing process inefficient.

Therefore, In a further embodiment the conduit comprises a tube arranged for length wise insertion into the repository and to displace powdered material from its path transversely to said insertion.

It is preferred that the conduit comprises a tube having a wall including a portion with a length wise tapered cross-sectional area. The cross-sectional perimeter of a portion of the tube can be tapered in a length wise direction. The cross-sectional area of a portion of the lumen defined by the tube can taper in a length wise direction. It is preferred that the cross-sectional area of the tube wall tapers towards an open end of the tube located within the repository. The open end can be in the form of an annular knife edge. Alternatively, the tube can be sealed to the repository excepting an opening, or openings, in its wall. Thus, when the conduit is forced downwards on the powdered material, the powdered material is more easily displaced, resulting in easy insertion of the conduit when the apparatus is in the upright position.

In a preferred embodiment the apparatus is arranged for the delivery of powdered material into a nasal cavity, this is preferably possible wherein the outlet forms a nozzle for insertion into a nostril.

In a further preferred embodiment the conduit is a dip tube.

Apparatus in accordance with the invention may dispense powdered material for the treatment of a medical condition, preferably for the treatment of allergic rhinitis or asthma and preferably wherein the powdered material is hydroxypropylmethylcellulose.

A further aspect of the invention is a conduit for use in the apparatus as described above.

In a yet further aspect of the present invention, there is provided a dip tube for use in apparatus for dispensing a restricted amount of powdered material, wherein the dip tube is arranged for length wise insertion into a repository and to displace is powdered material from its path transversely to said insertion.

It is preferred that the dip tube comprises a tube having a wall including a portion with a length wise tapered cross-sectional area. The cross-sectional perimeter of a portion of the tube can be tapered in a length wise direction. The cross-sectional area of a portion of the lumen defined by the tube can taper in a length wise direction. It is preferred that the cross-sectional area of the tube wall tapers towards an open end of the tube located within the repository. The open end can be in the form of an annular knife. Alternatively, the tube can be sealed to the repository excepting an opening, or openings, in its wall.

In a preferred embodiment of the invention a dip tube is arranged for the delivery of powdered material into a nasal cavity, this is preferably possible wherein the outlet forms a nozzle for insertion into a nostril.

A dip tube in accordance with the invention may dispense powdered material for the treatment of a medical condition, preferably for the treatment of allergic rhinitis or asthma wherein the powdered material is preferably hydroxypropylmethylcellulose.

An example of an apparatus according to the present invention will now be described, by way of example only, and will make reference to the following drawings.

Figure 1:
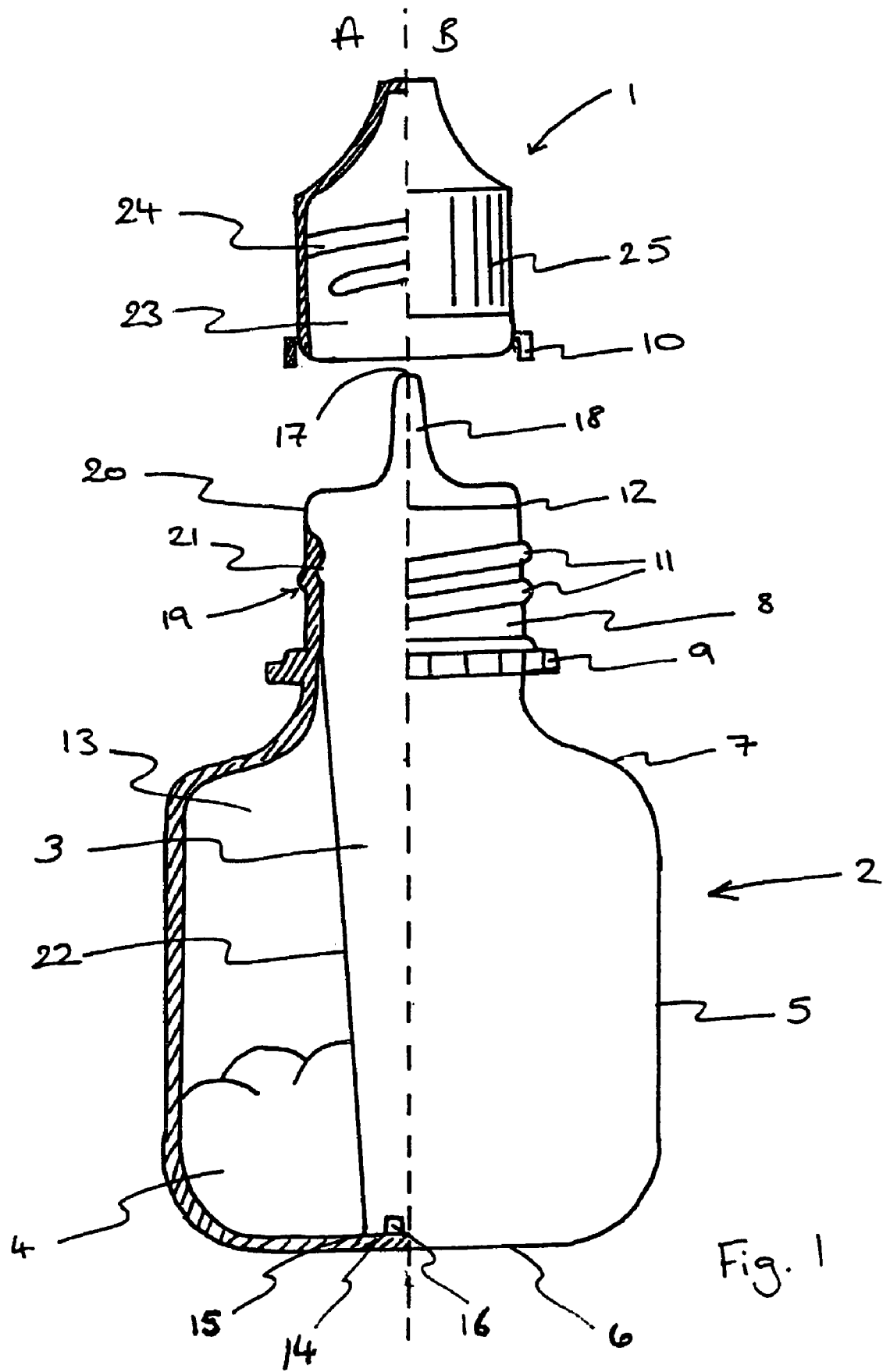
FIG. 1 shows a side plan view (side B), and section thereof (side A), of a nasal delivery apparatus in accordance with the invention.

Apparatus in accordance with the invention is shown in FIG. 1 and comprises a cap 1 and a bottle 2, formed from a thermal plastic material such as polyvinylchloride, housing a dip tube 3, and provides a repository for a quantity of powdered material 4. The cylindrical bottle 2 comprises a substantially cylindrical body portion 5, extending between a first end portion 6 and shoulder portion 7. The first end portion 6 defines a flat closed disc end base of the bottle 2. The bottle also comprises a neck portion 8, extending between the shoulder portion 7 and the second end portion 12 which defines an opening. A first annular flange 9 extends radially outward from the neck portion 8 of the cylindrical bottle 2 and is releaseably sealed with a second annular flange 10 disposed on the cap 1, to form in use, a tamper proof safety seal as would be readily known to a man skilled in the art. A first screw thread 11 commences at the first annular flange 9 and extends around and partway along the neck portion 8 of the cylindrical bottle 2 in the direction of the second end portion 12. The dip tube 3 is inserted into the internal cavity 13 of the bottle 2 through the opening defined by the second end portion 12, sealing said opening defined by the second end portion 12 by acting as a stopper for the bottle.

The dip tube 3 comprises a hollow tube with a first opening 14 at one end, opening into the internal cavity 13. The rim 15 defining the first opening 14 abuts with, or substantially abuts with, the internal surface of the first end portion 6. A castellation 16 defines a notch in the side wall of the dip tube 3, said notch defined by the castellation being continuous with the first opening 14. At the opposite end of the first opening 14 of the dip tube 3 is the second opening 17. The second opening 17 is disposed at the tip of the nozzle portion 18 of the dip tube 3. The nozzle portion 18 is a narrowed portion of the dip tube 3 such that it is dimensioned to fit up a nostril. The dip tube 3 has a radial protrusion 21 which fits inside an indentation on the inner surface of the neck portion 8 of the bottle 2 to form a friction fit. A further radial protrusion 20 on the dip tube 3 sits on top of the bottle neck to seal the bottle.

The cap 1 is shaped such that it may releasably retain the neck portion 8 and nozzle 18 within the cavity 23 when the devise is not in use. When not in use, first screw thread 11, co-operates with second screw thread 24, which is disposed on the internal surface of the cap 1. The cap 1 has a friction surface 25 extending around a portion of external surface of the cap, for ease of rotation between opposing fingers during the operation of removing the cap 1 from the bottle 2.

Figure 2:
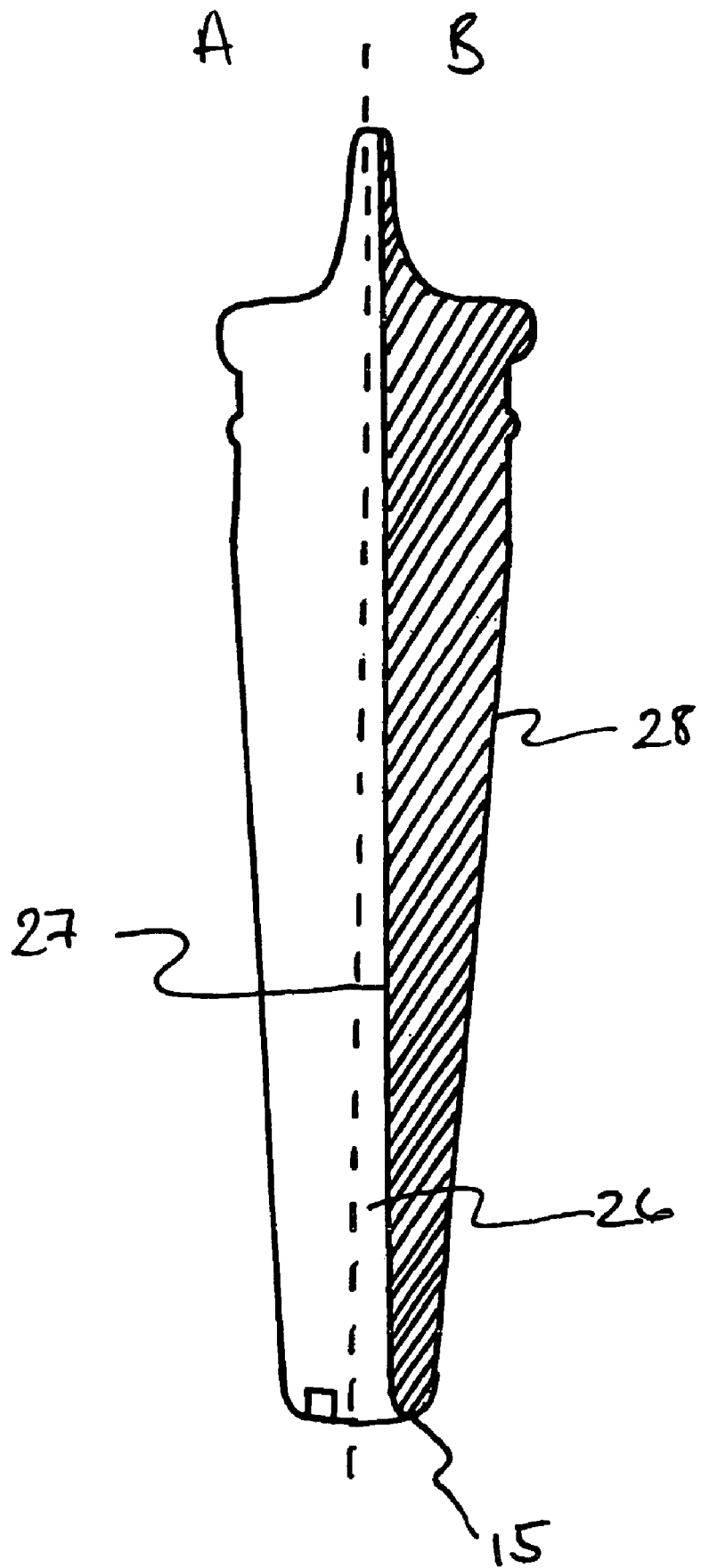
FIG. 2 shows a side plan view (side A), and sectional view thereof (side B), of a dip tube in accordance with the invention.

FIG. 2 shows a preferred embodiment of the dip tube 3. Side B of the dotted line shows a section through the dip tube 3. The dip tube 3 has a lumen 26 linking the first 14 and second 17 openings. The inner wall 27 and outer wall 28 become gradually closer, graduations occur in the portion of the dip tube 3 that is disposed within the body portion 5 of the bottle 2. This narrowing of the width of the wall results in a gradual reduction in the diameter of the dip tube 2 and an increase in the diameter of the lumen 26 within the dip tube 2. The narrowest point of the tapering portion 22 defines the first opening 14. At this point the inner wall and the outer wall meet to form the rim 15 of the first opening 14. The sectional profile of the rim 15 being rounded.

Figure 3:
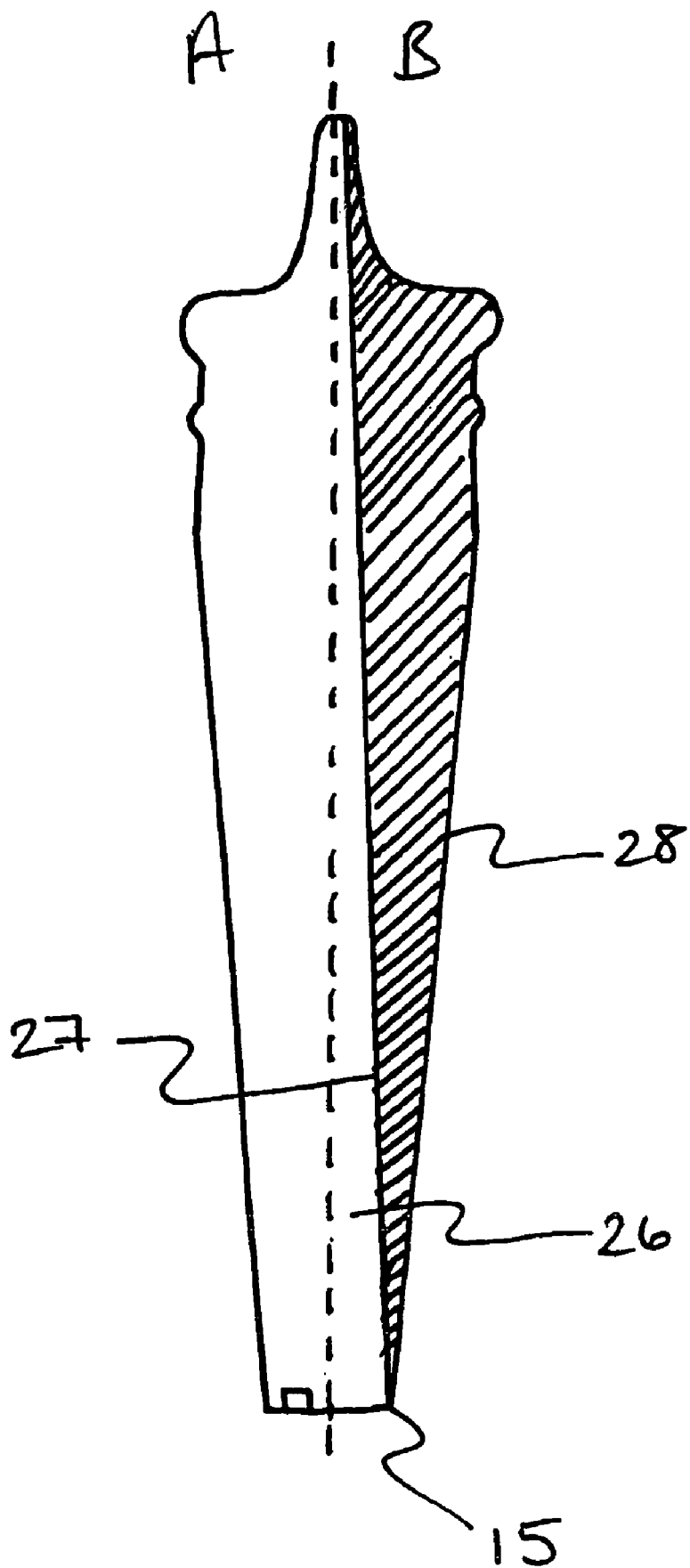
FIG. 3 shows a side plan view (side A), and a sectional view thereof (side B), of a dip tube in accordance with the invention.

In an alternative embodiment as shown in FIG. 3 the inner and outer walls taper to the first opening 14 with an inner wall 27 and outer wall 28 meeting to form a sharp point at the rim 15 in sectioned profile.

Figure 4:
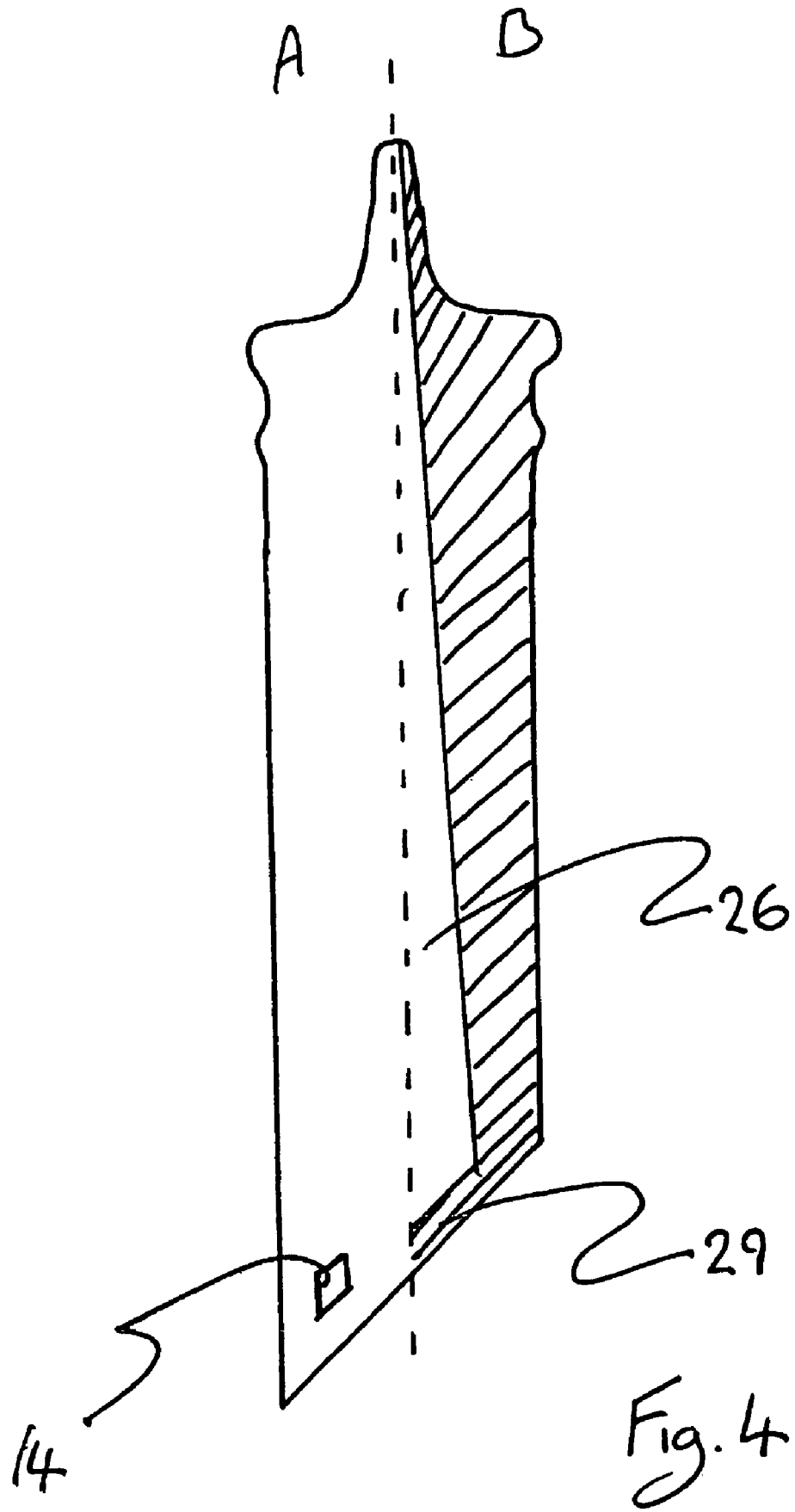
FIG. 4 shows a side plan view (side A), and a sectional view thereof (side B), of a dip tube in accordance with the invention.

In a further alternative embodiment, as shown in FIG. 4, the end of the tip tube 3, to be located in the internal cavity 13, is formed as if cut at an acute angle to the tube's axis and sealed with an eliptical end plate 29. A first opening 14 is formed in the side wall of the dip tube 3 adjacent to the plate 29.

In use, the cylindrical bottle 2 is filled with powered material 4. A user should place the nozzle 18 defining the second end portion 12 of the dip tube 3 into a nostril and then squeeze the body portion 5 between opposing fingers. The compression of the body portion 5 reduces the volume of the cylindrical bottle 2, thereby increasing internal pressure relative to atmospheric pressure. This results in a proportion of the air within the cylindrical bottle flowing down the pressure gradient and finding an exit by travelling through the castellation 16, up through the lumen 26 of the dip tube 3 and exiting at the second opening 17 into the nostril. As the air flows through the apparatus, particles of the powered material 4 will become entrained therein. The limited volume of the powder 4 that is capable of passage through castellation 16 whilst entrained in the air flow will be delivered to the nasal cavity. The pressure gradient will be transient, as equilibrium will be re-established rapidly. The transience of the air flow combined with the fact that the castellation 16 limits the amount of powered material 4 that is given passage to the lumen 26, results in a regulation of the powered material 4 that is capable of expulsion from the apparatus during a single compression of the body portion 5.

The invention claimed is:

1. An apparatus for dispensing a regulated amount of powdered material, comprising:
    a repository for powdered material, said repository having a compressible body portion, a first end forming a base of said body portion, and a second end opposite to said first end defining an outlet; and
    a hollow conduit connecting the interior of said repository to said outlet, said conduit arranged to extend from said first end of said repository to said outlet and comprising:
        a first opening defining an entrance to said conduit and in substantial abutment with an internal wall of said repository to seal said first opening; and
        a second opening adjacent to said first opening and in the wall of said conduit, said second opening defining a restriction that regulates the amount of powdered material delivered through said conduit to said outlet; and
    wherein said body portion of said repository is configured to be compressed such that a volume of air is propelled through powdered material resting in said repository, thereby entraining the powdered material and carrying the entrained powdered material in an upward direction through said conduit and out of said repository via said outlet, and wherein the entrained powdered material passes to said conduit from said repository through said second opening of said conduit.

2. The apparatus according to claim 1, wherein said second opening of said conduit is in the form of one or more notches in said conduit.

3. The apparatus according to claim 1 or 2, wherein said conduit is arranged for lengthwise insertion into said repository and to displace powdered material from its path transversely to said insertion.

4. The apparatus according to claim 3, wherein said conduit is a dip tube.

5. The apparatus according to claim 3, wherein a cross-sectional perimeter of a portion of said conduit is tapered in a lengthwise direction.

6. The apparatus according to claim 3, wherein a cross-sectional area of a portion of a lumen defined by said conduit tapers in a lengthwise direction.

7. The apparatus according to claim 5, wherein said cross-sectional area of said conduit tapers toward an end of said conduit which is located within said repository, said end of said conduit comprising said first opening of said conduit.

8. The apparatus according to claim 5, wherein an end of said conduit which is located within said repository is in the form of an annular knife edge, said end of said conduit comprising said first opening of said conduit.

9. The apparatus according to claim 1 or 2, wherein said second opening in said wall of said conduit is continuous with said first opening.

10. The apparatus according to claim 1 or 2, wherein said conduit is a dip tube.

11. The apparatus according to claim 1, wherein said conduit includes a portion with a lengthwise tapered cross-sectional area.

12. The apparatus according to claim 11, wherein a cross-sectional perimeter of a portion of said conduit is tapered in a lengthwise direction.

13. The apparatus according to claim 12, wherein said cross-sectional area of said conduit tapers toward an end of said conduit which is located within said repository, said end of said conduit comprising said first opening of said conduit.

14. The apparatus according to claim 12, wherein an end of said conduit which is located within said repository is in the form of an annular knife edge, said end of said conduit comprising said first opening of said conduit.

15. The apparatus according to claim 11, wherein said conduit is a dip tube.

16. The apparatus according to claim 1, said apparatus arranged for the delivery of powdered material into a nasal cavity.

17. The apparatus according to claim 16, wherein said outlet forms a nozzle for insertion into a nostril.

18. The apparatus according to claim 1, wherein the powdered material is for the treatment of a medical condition.

19. The apparatus according to claim 18, wherein the powdered material is for the treatment of allergic rhinitis or asthma.

20. The apparatus according to claim 18 or 19, wherein the powdered material is hydroxypropylmethylcellulose.

* * * * *